US006310235B1

(12) United States Patent
Gick

(10) Patent No.: US 6,310,235 B1
(45) Date of Patent: Oct. 30, 2001

(54) METHOD FOR PRODUCING ESTER PLASTICIZERS

(75) Inventor: Wilhelm Gick, Duisburg (DE)

(73) Assignee: Celanese GmbH (DE)

( * ) Notice: Subject to any disclaimer, the term of this patent is extended or adjusted under 35 U.S.C. 154(b) by 0 days.

(21) Appl. No.: 09/424,124

(22) PCT Filed: May 16, 1998

(86) PCT No.: PCT/EP98/02899

§ 371 Date: Nov. 17, 1999

§ 102(e) Date: Nov. 17, 1999

(87) PCT Pub. No.: WO98/52901

PCT Pub. Date: Nov. 26, 1998

(30) Foreign Application Priority Data

May 22, 1997 (DE) .............................. 197 21 347

(51) Int. Cl.[7] .................................................. C07C 67/08
(52) U.S. Cl. .............................. 560/99; 560/78; 560/98; 560/103; 560/204; 560/232
(58) Field of Search .................................. 560/99, 78, 98, 560/204, 103, 232

(56) References Cited

U.S. PATENT DOCUMENTS 5,434,294 * 7/1995 Pugach et al. .

FOREIGN PATENT DOCUMENTS 1945359 3/1971 (DE) .
1426057 2/1976 (GB) .

* cited by examiner

Primary Examiner—Gary Geist
Assistant Examiner—Robert W. Deemie
(74) Attorney, Agent, or Firm—Bierman, Muserlian and Lucas

(57) ABSTRACT

The invention relates to an improved method for producing ester plasticizers by reacting di- or polycarboxylic acids or their anhydrides with alcohols in the presence of metal catalysts.

10 Claims, No Drawings

METHOD FOR PRODUCING ESTER PLASTICIZERS

This application is a 371 of PCT/EP98/02899 filed May 16, 1998.

The invention relates to a process for preparing ester plasticizers from dicarboxylic or polycarboxylic acids or their anhydrides and alcohols by reacting the starting materials in the presence of metal catalysts.

Plasticizers are widely used in many ways in plastics, coating compositions, sealing compositions and rubber articles. They interact physically with thermoplastic high polymers without reacting chemically, preferably by means of their solvent and swelling capability. This forms a homogeneous system whose thermoplastic range has been shifted to lower temperatures compared to the original polymer, with the result that, for example, the ability to change shape and the elasticity are increased and the hardness is reduced.

To open up very wide fields of application for plasticizers, they have to fulfil a number of requirements. In the ideal case, they should be odorless, colorless, light-resistant, cold-resistant and heat-resistant. In addition, it is expected that they are resistant to water, do not burn readily, have a low volatility and are not harmful to health. Furthermore, the preparation of the plasticizers should be simple and, to meet ecological demands, should be carried out without producing waste materials such as by-products which cannot be recycled and wastewater containing pollutants.

Among the most important plasticizers are the esters of dicarboxylic and polycarboxylic acids with plasticizer alcohols, i.e. unbranched or branched primary alcohols having from about 6 to 13 carbon atoms, which can be used as individual compounds or as a mixture. The preparation of the esters has been carried out by the classical process by reacting the acids or acid anhydrides with an alcohol or a mixture of different alcohols in the presence of an acid, preferably sulfuric acid, as catalyst. The alcohol component is usually used in excess. Attempts have been made to counter adverse color and odor of the reaction product by targeted selection of the acid used as catalyst, by mild reaction conditions and by complicated purification measures.

A further development in the preparation of esters suitable as plasticizers constitutes the use of metal-containing esterification catalysts. Suitable catalysts are, for example, tin, titanium and zirconium which are used as finely divided metals or advantageously in the form of their salts, oxides or soluble organic compounds. These catalysts are high-temperature catalysts which reach their full activity only at esterification temperatures above 180° C. Examples are tin powder, tin(II) oxide, tin(II) oxalate, titanate esters such as tetraisopropyl orthotitanate or tetrabutyl orthotitanate and also zirconium esters such as tetrabutyl zirconate. Alkyl titanates and titanium chelates, i.e. titanates of polyalcohols, have achieved particular importance in industrial production processes. One such method is, for example, subject matter of the U.S. Pat. No. 5,434,294 and is also described in DE 19 45 359.

Furthermore, EP-A-0 424 767 discloses a process for the esterification of phthalic anhydride with isodecanol in the presence of tetrabutyl titanate as catalyst at 230° C. Subsequent to the esterification, the reaction mixture is treated with sodium carbonate solution and the excess alcohol is distilled off. The treatment with the sodium carbonate solution neutralizes the phthalic monoesters present in the reaction mixture to form the corresponding salts. These salts are obtained as a slimy precipitate which can be filtered off only with difficulty, necessitating a high outlay in terms of time and apparatus. Obtaining the desired phthalic diester in pure form is thus associated with considerable difficulties.

The modern processes for preparing ester plasticizers thus do not yet fulfil all aspects of the above-described demands made of the production process and the reaction product.

It is therefore an object of the invention to improve the known processes and, by matching and simplifying the successive substeps of the entire process, to optimize the process and to simplify the isolation of the reaction product in high quantity so that this reaction product can be employed in as many applications as possible.

The invention provides a process for preparing ester plasticizers by reacting dicarboxylic or polycarboxylic acids or their anhydrides with alcohols in the presence of a titanium-, zirconium- or tin-containing catalyst. It comprises allowing a mixture of acid or acid anhydride and alcohol to react first at from 100 to 160° C. while removing any water formed, completing the reaction by addition of the catalyst and increasing the temperature to about 250° C., neutralizing the reaction mixture with an aqueous alkali metal hydroxide or alkaline earth metal hydroxide solution, then separating off the excess alcohol and drying and filtering the remaining crude ester.

The novel process has high reliability when implemented in industrial plants. It is easy to carry out, including continuously, and gives plasticizers of high purity. The problem-free and complete removal of the monoester formed as by-product during the reaction, the catalyst present in the reaction mixture and the reagents used for neutralization is particularly note-worthy. The complete removal of these by-products and auxiliaries results, inter alia, in the excellent color properties as well as the remarkable color stability of the process products. Also worth emphasizing is their extremely low conductivity which makes it possible to use them widely for plastics in the field of cable insulation.

Acids suitable as starting materials for the process of the invention are aliphatic and aromatic dicarboxylic and polycarboxylic acids. The aliphatic carboxylic acids can be saturated or unsaturated and contain at least four carbon atoms. Examples of such compounds are succinic acid, glutaric acid, adipic acid, suberic acid, azelaic acid, maleic acid and fumaric acid. Examples of the aromatic carboxylic acids are, in particular, phthalic acid and trimellitic acid. The acids can be used either in pure form or in the form of mixtures. In place of the acids, their anhydrides can also be successfully employed.

Alcohols used are, in particular, straight-chain or branched saturated aliphatic compounds having more than 6 carbon atoms in the molecule. They usually contain a primary hydroxyl group, but secondary alcohols are not ruled out as reaction partners of the acids. Examples of such compounds are 1-n-octanol, 2-n-octanol, 2-ethylhexan-1-ol, n-nonyl alcohol, decyl alcohol and the so-called oxo alcohols, i.e. mixtures of straight-chain and branched alcohols of corresponding molecular size which are obtained from olefins by the oxo process and subsequent hydrogenation. The alcohols too can be employed as pure compounds or as mixtures of structurally isomeric compounds or compounds of different molecular size.

The new method has been found to be particularly useful for preparing esters of phthalic acid with $C_8$–$C_{12}$-alcohols and, among these, in particular for preparing di(2-ethylhexyl)phthalate.

Esterification catalysts used in the novel process are titanium, zirconium or tin as metals in finely divided form or, preferably as compounds. Suitable compounds are tin (II) oxide, tin (II) oxalate, phenoxides, acylates and chelates of titanium and zirconium and also esters of titanium and of zirconium, e.g. tetra-(isopropyl) orthotitanate, tetrabutyl orthotitanate and tetrabutyl zirconate. The amount of catalyst used can extend over a wide range. It is possible to use both 0.01% by weight and also more than 5% by weight of catalyst, based on the reaction mixture. However, since larger amounts of catalyst give hardly any advantages, the catalyst concentration is usually from 0.01 to 1.0% by weight, preferably from 0.01 to 0.5% by weight, in each case based on the reaction mixture.

Although the esterification can be carried out using stoichiometric amounts of alcohol and acid, particularly when entrainers are used for removing the water of reaction, preference is given to using a stoichiometric excess of the alcohol of from 0.05 to 0.6 mole per mole of dicarboxylic or polycarboxylic acid or acid anhydride in order to achieve as complete as possible a conversion of the acid.

According to the invention, the esterification is carried out in two stages. In the first stage, without addition of a catalyst, the monoester of the dicarboxylic acid is formed. The temperatures to be employed in this stage depend largely on the starting materials. Satisfactory reaction rates are achieved above about 100° C. and preferably above 120° C. It is possible to complete the monoester formation at these temperatures. However, it is more advantageous to increase the temperature continuously up to about 160° C. When using carboxylic acids (rather than carboxylic anhydrides) as esterification component, the water formed is removed from the reaction system as an azeotrope with the alcohol, as long as the reaction temperature is above the boiling point of the azeotrope (i.e. in a range from 90 to 100° C. under atmospheric pressure). The course and completion of the esterification can in this case be observed via the formation of water. The use of subatmospheric or superatmospheric pressure is not ruled out, but will be restricted to special cases. To suppress the occurrence of concentration differences, it is advisable to stir the reactor contents or to mix them from time to time, e.g. by passing an inert gas through the reaction mixture.

In the second stage, the esterification of the dicarboxylic or polycarboxylic acids is completed. It is a carried out in the presence of the above-described catalysts at temperatures which are above those employed in the first stage and go up to about 250° C. This temperature is a guideline value which is advantageously employed. Lower temperatures can be sufficient, for example if in a specific case a sufficiently high reaction rate is achieved or only partial conversions are sought. Higher temperatures can be employed if the occurrence of decomposition products which, inter alia, have an adverse effect on the color can be ruled out. The reaction is advantageously carried out at the boiling point of the alcohol used. It can be carried out in a single reactor or also in the reaction vessel of the first stage. Water formed during the reaction is removed as an azeotrope, with the alcohol taking over the role of the entrainer. In this reaction stage too, it is advisable to mix the reactor contents at least from time to time in order to even out concentration differences and to accelerate the removal of the water of reaction.

After the reaction is complete, the reaction mixture comprises not only the desired reaction product, viz. the diester or polyester, but also, in particular, partially esterified dicarboxylic or polycarboxylic acids, excess alcohol and the catalyst.

To work up the crude ester plasticizer, the product from the reactor is first neutralized with alkali metal hydroxide or alkaline earth metal hydroxide. The alkaline reagent is here employed as an aqueous solution containing from 5 to 20% by weight, preferably from 10 to 15% by weight, of the hydroxide, based on the solution. The amount of neutralizing agent to be used depends on the proportion of acid components, free acid and monoesters in the crude product. This proportion is determined in the form of the acid number (in accordance with DIN 53169). According to the invention, the alkaline reagent is added in an excess which corresponds to from two to four times the amount which is stoichiometrically required to neutralize the $H^+$ ions present. The use of the selected hydroxides, among which sodium hydroxide has been found to be particularly useful, as aqueous solution having a particular concentration and in a defined excess ensures that the acidic constituents of the reaction mixture are precipitated in a crystalline, very readily filterable form. At the same time, the catalyst is largely decomposed to form likewise easily filterable products. The alkaline treatment of the crude ester is not tied to the maintenance of particular temperatures. It is advantageously carried out immediately after the esterification step without prior cooling of the reaction mixture.

The excess of alkali metal hydroxide or alkaline earth metal hydroxide, which is only a small amount relative to the reaction product, reacts with the ester to form a carbonate salt which is obtained in crystalline form and can be filtered off without difficulty.

Subsequent to the neutralization, the free alcohol is separated from the reaction mixture. Steam distillation has been found to be useful for this step and can be carried out in simple form by passing steam into the crude product. An advantage of steam distillation is that last residues of catalyst are destroyed during it and converted into conveniently filterable hydrolysis products. For this purpose, it can be advantageous to add a high surface area adsorbent, e.g. activated carbon, to the reaction mixture prior to the distillation in order to aid the removal of the downstream products of the catalyst.

The removal of the free alcohol is followed by the drying of the ester. In a particularly simple and effective embodiment of this step, drying is achieved by passing an inert gas through the product. The crude ester is then filtered to free it of solids, viz. the salts of (possibly partially esterified) carboxylic acids, hydrolysis products of the catalyst and the adsorbent. The filtration is carried out in conventional filtration equipment at room temperature or at temperatures up to 150°C. The filtration can also be aided by customary filter aids such as cellulose, silica gel, kieselguhr or wood flour. However, their use is restricted to exceptional cases.

The process of the invention drastically reduces the time required for separating off the solids present in the crude ester to values which ensure that it can be carried out economically on an industrial scale and avoids the formation of ecologically harmful wastewater, both in terms of amount and composition.

The esters obtained by the process claimed have excellent quality which fulfils even high requirements in every respect.

What is claimed is:

1. A process for preparing ester plasticizers by reacting dicarboxylic or polycarboxylic acids or their anhydrides with alcohols in the presence of a titanium-, zirconium- or tin-containing catalyst, which comprises allowing a mixture of acid or acid anhydride and alcohol to react first at from 100 to 160° C. while removing any water formed, completing the reaction by addition of the catalyst and increasing the temperature to about 250° C., neutralizing the reaction mixture with an aqueous alkali metal hydroxide or alkaline earth metal hydroxide solution, then separating off the excess alcohol and drying and filtering the remaining crude ester.

2. The process as claimed in claim 1, wherein the catalyst is tetra(isopropyl) orthotitanate, tetrabutyl orthotitanate or tetrabutyl zirconate.

3. The process as claimed in claim 1, wherein the alcohol is used in a stoichiometric excess of from 0.05 to 0.6 mole per mole of dicarboxylic or polycarboxylic acid.

4. The process as claimed in claim 1, wherein water of reaction formed during the reaction is removed from the reaction mixture as an azeotrope with the alcohol used.

5. The process as claimed in claim 1, wherein the reaction is completed at the boiling point of the alcohol used.

6. The process as claimed in claim 1, wherein the alkali metal hydroxide or alkaline earth metal hydroxide solution employed for neutralizing the reaction mixture contains from 5 to 20% by weight, of hydroxide, based on the solution.

7. The process as claimed in claim 1, wherein the alkali metal hydroxide or alkaline earth metal hydroxide solution is employed in an excess which corresponds to from two to four times the amount which is stoichiometrically required to neutralize the $H^+$ ions present in the reaction mixture.

8. The process of claim 1, wherein excess alcohol is separated from the reaction mixture by steam distillation optionally in the presence of an adsorbent.

9. The process as claimed in claim 1, wherein phthalic acid and 2-ethylhexanol as starting materials are reacted with one another.

10. The process of claim 6 wherein the hydroxide solution contains 10 to 15% by weight of hydroxide.

* * * * *